United States Patent
Hu et al.

(10) Patent No.: US 10,685,737 B2
(45) Date of Patent: Jun. 16, 2020

(54) AUTOMATICALLY IDENTIFYING STATISTICALLY SIGNIFICANT COMBINATION THERAPIES FROM CLINICAL DATA

(71) Applicant: International Business Machines Corporation, Armonk, NY (US)

(72) Inventors: Gang Hu, Beijing (CN); Xiang Li, Beijing (CN); Haifeng Liu, Beijing (CN); Guo Tong Xie, Beijing (CN); Ping Zhang, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 350 days.

(21) Appl. No.: 15/667,237

(22) Filed: Aug. 2, 2017

(65) Prior Publication Data

US 2019/0042691 A1 Feb. 7, 2019

(51) Int. Cl.
| | | |
|---|---|---|
| *G01N 33/48* | (2006.01) | |
| *G01N 33/50* | (2006.01) | |
| *G16B 20/00* | (2019.01) | |
| *G06F 19/00* | (2018.01) | |
| *G16H 50/30* | (2018.01) | |
| *G16H 50/50* | (2018.01) | |
| *G16H 20/10* | (2018.01) | |
| *G16H 50/70* | (2018.01) | |
| *G16B 25/00* | (2019.01) | |
| *G16B 40/00* | (2019.01) | |

(52) U.S. Cl.
CPC ......... *G16B 20/00* (2019.02); *G06F 19/3456* (2013.01); *G16H 20/10* (2018.01); *G16H 50/30* (2018.01); *G16H 50/50* (2018.01); *G16H 50/70* (2018.01); *G16B 25/00* (2019.02); *G16B 40/00* (2019.02)

(58) Field of Classification Search
None
See application file for complete search history.

(56) References Cited

U.S. PATENT DOCUMENTS

| | | | |
|---|---|---|---|
| 9,342,657 B2 | 5/2016 | Wei | |
| 2005/0176072 A1* | 8/2005 | Martin | G01N 33/574 435/7.23 |
| 2008/0262804 A1* | 10/2008 | Howard | G06Q 10/10 703/2 |
| 2014/0025310 A1 | 1/2014 | Winters | |
| 2015/0106112 A1 | 4/2015 | Jackson et al. | |

\* cited by examiner

*Primary Examiner* — Russell S Negin
(74) *Attorney, Agent, or Firm* — Scully, Scott, Murphy & Presser, P.C.; Joseph Petrokaitis, Esq.

(57) ABSTRACT

Combination therapies are automatically discovered that provide statistically significantly greater protection against a specific outcome, compared to therapies with fewer treatments. A dataset is received that associates each of a plurality of respective individual treatments with a corresponding outcome and a corresponding set of confounding factors. A plurality of new potential combination therapies are combined iteratively. The received dataset is used to automatically identify at least one candidate combination therapy of the new potential combination therapies that provides a statistically significantly greater protection against an outcome with reference to each of the plurality of respective individual treatments.

12 Claims, 6 Drawing Sheets

FIG. 1

| PATIENT ID 201 | PCI 203 | STATINS 205 | ASPIRIN 207 | HEPARIN 209 | NITRATES 211 | ORAL ASIAN MEDICINE 213 | AGE 215 | ... | ... | GENDER 217 | ... | ... | OUTCOME ID (LIVING OR DEAD) 219 |
|---|---|---|---|---|---|---|---|---|---|---|---|---|---|
| 1 | 1 | 1 | 0 | 1 | 0 | 0 | 74 | ... | ... | 0 | ... | ... | 0 |
| 2 | 0 | 1 | 1 | 1 | 1 | 0 | 69 | ... | ... | 1 | ... | ... | 0 |
| 3 | 1 | 0 | 1 | 0 | 0 | 1 | 82 | ... | ... | 1 | ... | ... | 1 |
| 4 | 1 | 1 | 1 | 1 | 1 | 0 | 73 | ... | ... | 0 | ... | ... | 1 |
| 5 | 0 | 0 | 1 | 0 | 0 | 0 | 54 | ... | ... | 0 | ... | ... | 0 |
| 6 | 1 | 0 | 1 | 0 | 0 | 0 | 68 | ... | ... | 1 | ... | ... | 1 |
| 7 | 1 | 1 | 1 | 1 | 1 | 0 | 75 | ... | ... | 0 | ... | ... | 0 |
| 8 | 0 | 1 | 0 | 1 | 0 | 1 | 89 | ... | ... | 1 | ... | ... | 1 |
| 9 | 1 | 0 | 1 | 1 | 1 | 0 | 70 | ... | ... | 1 | ... | ... | 0 |
| ... | ... | ... | ... | ... | ... | ... | ... | ... | ... | ... | ... | ... | ... |

| PATIENT ID 201 | PCI 203 | STATINS 205 | ASPIRIN 207 | HEPARIN 209 | NITRATES 211 | ORAL ASIAN MEDICINE 213 | AGE 215 | GENDER 217 | A vs. B | OUTCOME ID (LIVING OR DEAD) 219 |
|---|---|---|---|---|---|---|---|---|---|---|
| 1 | 1 | 1 | 0 | 1 | 0 | 0 | 74 | 0 | 1 | 0 |
| 2 | 0 | 1 | 1 | 1 | 1 | 0 | 69 | 1 | 0 | 0 |
| 3 | 1 | 0 | 1 | 0 | 0 | 1 | 82 | 1 | 1 | 1 |
| 4 | 1 | 1 | 1 | 1 | 1 | 0 | 73 | 0 | 0 | 1 |
| 5 | 0 | 0 | 1 | 0 | 0 | 0 | 54 | 0 | 1 | 0 |
| 6 | 1 | 0 | 1 | 1 | 1 | 0 | 68 | 1 | 1 | 1 |
| 7 | 1 | 1 | 1 | 1 | 0 | 0 | 75 | 0 | 0 | 0 |
| 8 | 0 | 1 | 0 | 1 | 1 | 1 | 89 | 1 | 1 | 1 |
| 9 | 1 | 0 | 1 | 1 | 0 | 0 | 70 | 1 | 0 | 0 |
| ... | ... | ... | ... | ... | ... | ... | ... | ... | ... | ... |

401, 402, 401, 402, 403, 404

| | SURVIVED 412 | DEAD 413 |
|---|---|---|
| A = PCI + STATINS | TP | FP |
| B = PCI WITHOUT STATINS | FN | TN |

AUTOMATICALLY IDENTIFYING STATISTICALLY SIGNIFICANT COMBINATION THERAPIES FROM CLINICAL DATA

FIELD

The present application relates generally to systems and methods for bioinformatics and data processing and, more specifically, to processes and systems that automatically identify statistically significant combination therapies from clinical data.

BACKGROUND

Combination therapy with multiple interventions may provide greater treatment or protection against a specific outcome relative to using single-intervention therapies. In clinical research, it is very difficult to raise reasonable hypotheses of new potential combination therapies from clinical experience. It is also very difficult to test all candidate combination therapies due to the sheer number of numerical combinations that are involved when considering a wide range of multiple interventions. Existing association rule mining methods can discover co-occurrence patterns that are frequently satisfied and that are more likely to lead to positive or negative outcomes. However, these methods are not equipped to compare the effectiveness of a proposed multiple-intervention combination therapy against that of a counterpart therapy which uses a lesser number of interventions relative to the proposed therapy.

BRIEF SUMMARY

The following summary is merely intended to be exemplary. The summary is not intended to limit the scope of the claims.

One embodiment of the present invention is a computer-implemented method for receiving a dataset associating each of a plurality of respective individual treatments with a corresponding outcome and a corresponding set of confounding factors; iteratively combining a plurality of new potential combination therapies; and using the received dataset to automatically identify at least one candidate combination therapy of the new potential combination therapies that provides a statistically significantly greater protection against an outcome with reference to each of the plurality of respective individual treatments.

Other embodiments include a computer program product and a computer system.

BRIEF DESCRIPTION OF THE SEVERAL VIEWS OF THE DRAWINGS

The foregoing aspects and other features are explained in the following description, taken in connection with the accompanying drawings, wherein.

DETAILED DESCRIPTION

Combination therapy with multiple interventions may provide greater treatment or protection against specific outcomes than single interventions. For example, combination therapy comprising clopidogrel and aspirin may be more effective at treating a stroke compared to using aspirin alone. More than two interventions, such as clopidogrel, aspirin, and a statin drug, can be used as combination therapy.

The process for proposing a new combination therapy may involve four steps. First, a hypothesis of a new combination therapy is formulated from clinical experience. Second, clinical data of interest is collected. This data may include real-world data as well as data from randomized controlled trials. Third, a univariate analysis is performed to compare an impact of the new combination therapy on a therapy outcome with an impact of an existing therapy on the therapy outcome. Fourth, for any therapy that has a statistically significant impact on the therapy outcome in the univariate analysis (such as a p-value <0.05), a multivariate analysis is performed to consider one or more confounding factors.

The most difficult task in proposing a new combination therapy is the formulation of a reasonable hypothesis. Only clinicians with rich clinical experience can summarize new potential combination therapy from a wide range of different medications. Moreover, many of these hypotheses cannot be proved by real world clinical data. Sometimes the real world data provide opposing or contradictory results, or the results may not be statistically significant. It is virtually impossible to test all candidate combination therapies due to the sheer number of numerical combinations that are involved when considering a wide range of multiple interventions.

Existing association rule mining methods have been employed to propose new combination therapies by discovering co-occurrence patterns that were frequently satisfied, and that were more likely to lead to positive (or negative) outcomes. Unfortunately, the relationship between a therapy and its outcome are measured using confidence, where the outcome of not using the therapy (or using the therapy with less interventions) is not considered and compared. In addition, the significance of the mined patterns, which is very important for combination therapy to be accepted, cannot be ensured. Likewise, confounding factors are not considered which may lead to bias in the results.

Figure 1:
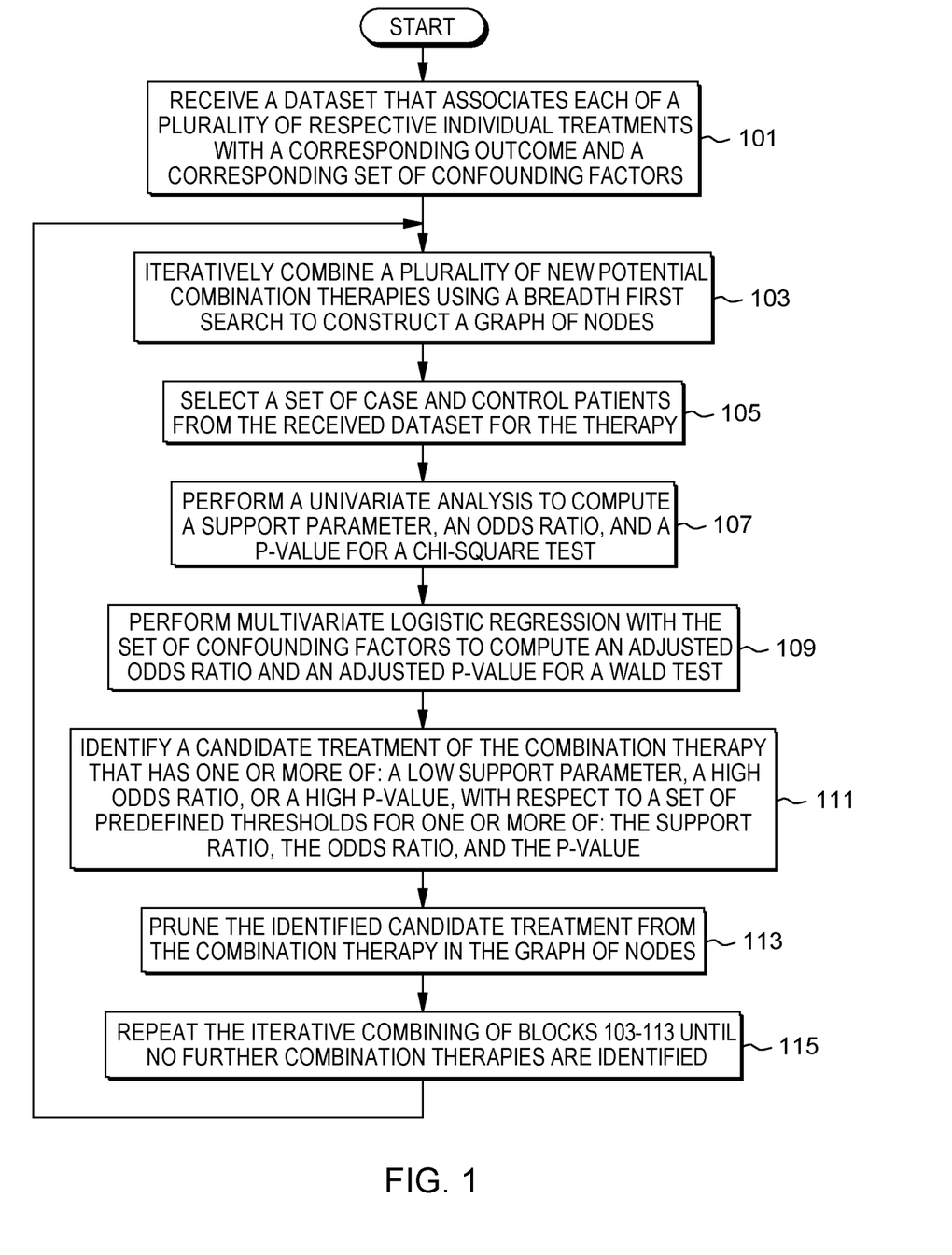
FIG. 1 illustrates an exemplary method for automatically identifying a statistically significant combination therapy from clinical data in accordance with one or more embodiments of the present invention.

FIG. 1 illustrates an exemplary method for automatically identifying a statistically significant combination therapy from clinical data in accordance with one or more embodiments of the present invention. The operational sequence commences at block 101 where a dataset is received that associates each of a plurality of respective individual treatments with a corresponding outcome and a corresponding set of confounding factors. Next, at block 103, a plurality of new potential combination therapies is iteratively combined using a breadth first search to construct a graph of nodes. The iterative combining comprises a plurality of iterations, where each iteration includes generating a node for combination therapy by adding one treatment to a therapy in a previous iteration or, when no previous iteration exists, adding an initial treatment to the therapy.

The operational sequence advances to block 105 where a set of case and control patients is selected from the received dataset for the therapy. Then at block 107, a univariate analysis is performed to compute a support parameter, an odds ratio, and a p-value for a Chi-square test. Univariate analysis refers to a data analysis procedure where the data has only one variable. This analysis does not deal with causes or relationships, but rather its purpose is to take in data, describe the data, summarize the data, and find patterns in the data. Multivariate logistic regression is performed at block 109 with the set of confounding factors to compute an adjusted odds ratio and an adjusted p-value for a Wald test. Multivariate data analysis refers to any statistical technique used to analyze data that arises from more than one variable. The Wald test is a parametric statistical test named after the Hungarian statistician Abraham Wald. Whenever a relationship within or between data items in the dataset can be expressed as a statistical model with a plurality of parameters to be estimated from a sample, the Wald test can be used to test for a true value of a parameter of the plurality of parameters based upon the sample estimate.

At block 111, a candidate treatment of the combination therapy is identified that has at least one of: a low support parameter, a high odds ratio, or a high p-value with respect to a set of predefined thresholds for one or more of: the support parameter, the odds ratio, or the p-value. The identified candidate treatment is pruned from the combination therapy of the graph of nodes at block 113. Then, the iterative combining is repeated at block 115 until no further combination therapies can be identified.

Figure 2:
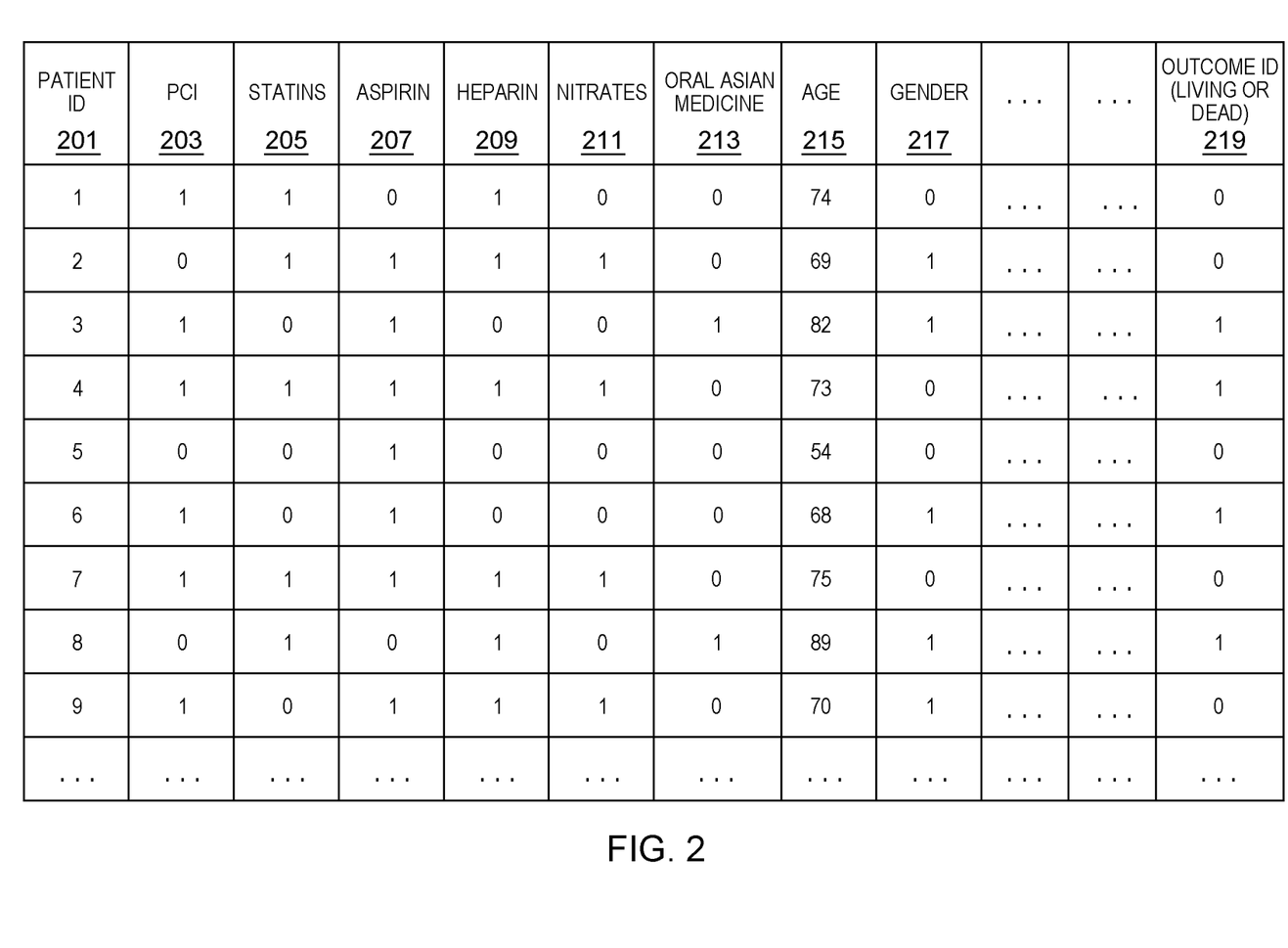
FIG. 2 illustrates an exemplary received dataset for use with the method of FIG. 1 in accordance with one or more embodiments of the present invention.

FIG. 2 illustrates an exemplary received dataset for use with the method of FIG. 1 in accordance with one or more embodiments of the present invention. The dataset associates each of a plurality of patient identifiers (IDs) 201 (FIG. 2) in a first column with a corresponding plurality of individual treatments, an outcome, and a plurality of confounding factors. In the example of FIG. 2, the individual treatments include percutaneous coronary intervention (PCI) 203, statins 205, aspirin 207, heparin 209, nitrates 211, and oral Asian medicine 213. The outcome comprises an outcome identifier (ID) 219 that specifies whether the patient identified by the patient ID 201 is still alive, or whether this patient is deceased. The confounding factors include age 215 and gender 217.

Figure 3:
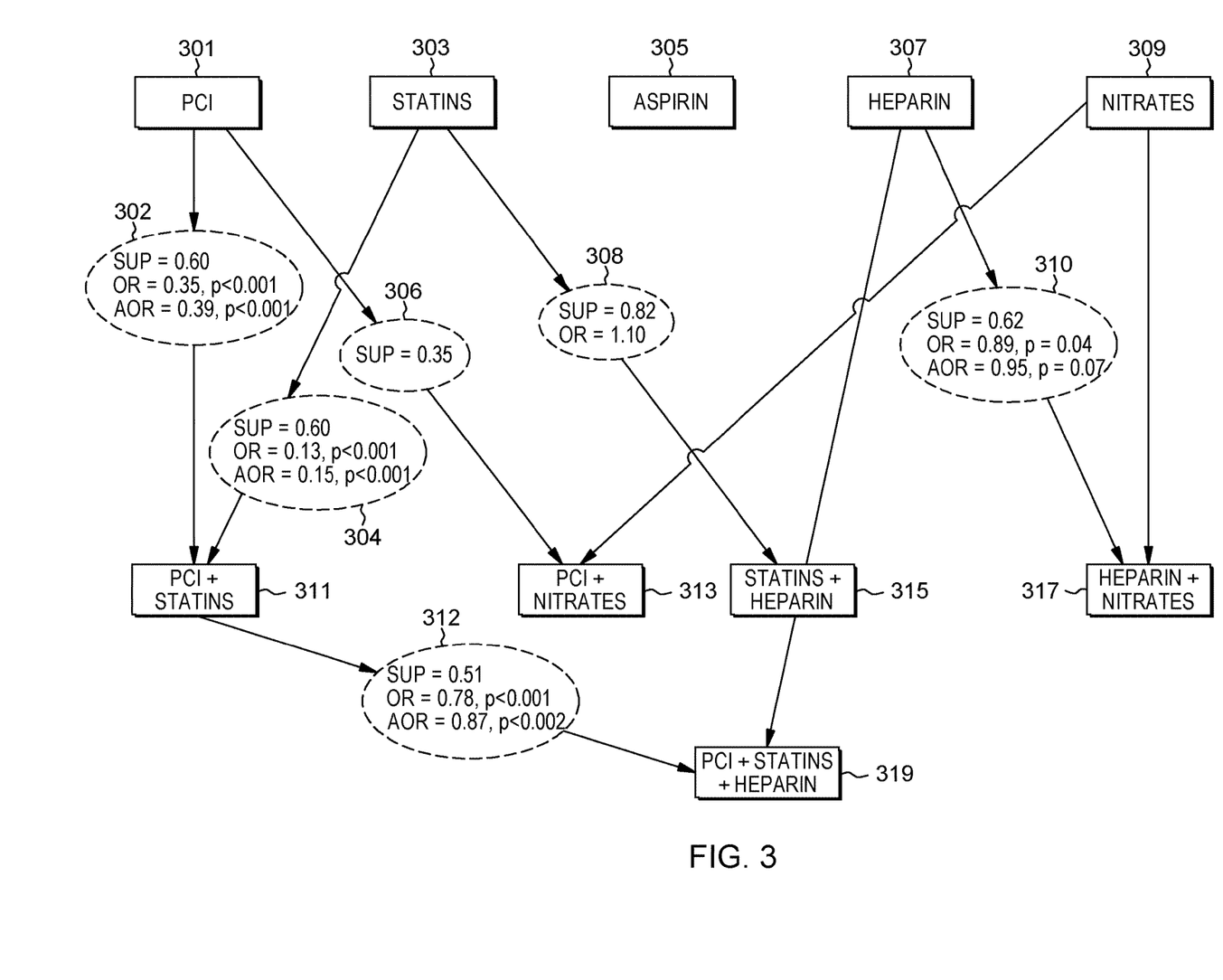
FIG. 3 illustrates an exemplary graph of nodes for use with the method of FIG. 1 in accordance with one or more embodiments of the present invention.

FIG. 3 illustrates an exemplary graph of nodes for use with the method of FIG. 1 in accordance with one or more embodiments of the present invention. As previously mentioned in connection with block 103, a plurality of new potential combination therapies is iteratively combined using a breadth first search to construct a graph of nodes. The iterative combining comprises a plurality of iterations, where each iteration includes generating a node for combination therapy by adding one treatment to a therapy in a previous iteration or, when no previous iteration exists, adding an initial treatment to the therapy. For example, assuming that no previous iteration exists, the graph of nodes may be constructed in a first iteration by adding several initial treatments to the therapy, including a first initial node 301 (FIG. 3) for PCI, a second initial node 303 for statins, a third initial node 305 for aspirin, a fourth initial node 307 for heparin, and a fifth initial node 309 for nitrates.

Next, nodes are generated for combination therapy by adding one treatment to a therapy in a previous iteration. A breadth first search strategy is used to generate nodes for combination therapies with k size that satisfies a set of constraints (to be discussed in greater detail hereinafter), by adding one treatment to the therapies with k−1 size in each iteration. For example, in a second iteration, a first combination node 311 is constructed for a first combination therapy of PCI plus statins. A second combination node 313 is constructed for a second combination therapy of PCI plus nitrates, a third combination node 315 is constructed for a third combination therapy of statins plus heparin, and a fourth combination node 317 is constructed for a fourth combination therapy of heparin plus nitrates. Then, in a third iteration, a fifth combination node 319 is constructed for a combination therapy of PCI plus statins plus heparin.

Figure 4:
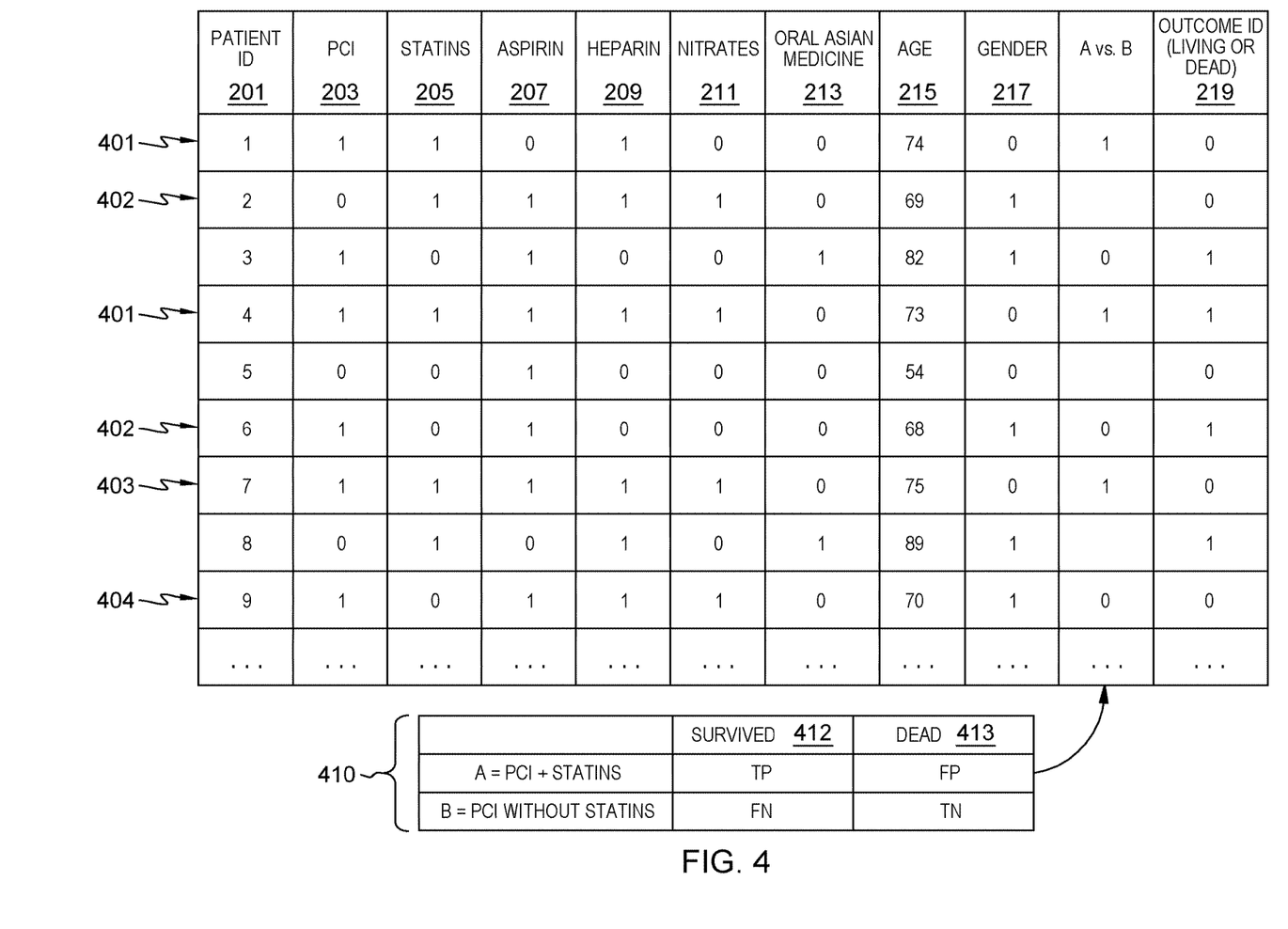
FIG. 4 illustrates an exemplary processing of the received dataset of FIG. 1 to construct the first exemplary graph of FIG. 3 in accordance with one or more embodiments of the present invention.

FIG. 4 illustrates an exemplary processing of the received dataset of FIG. 1 to construct the first exemplary graph of FIG. 3 in accordance with one or more embodiments of the present invention. Each of the combination nodes 311, 313, 315, 317 and 319 is constructed by selecting a case and control patient set for the therapy, such as a first case and control patient set 401 (FIG. 4), a second case and control patient set 402, and a third case and control patient set 403. A feature for combination therapy is generated for a combination node of the combination nodes 311, 313, 315, 317 and 319 (FIG. 3) by comparing the combination node with a parent node comprising any of the initial nodes 301, 303, 305, 307, and 309. This comparison may be performed using a comparison table 410 (FIG. 4) that compares a combination node, such as the first combination node 311 (FIG. 3), with an initial node, such as the first initial node 301.

The first combination node 311 represents a combination treatment A that includes PCI plus statins. The first initial node 301 represents a treatment B that includes PCI only, without statins. A treatment outcome of survived 412 (FIG. 4) is compared against a treatment outcome of dead 413. The treatment outcome of survived 412 for combination treatment A is designated as TP, the treatment outcome of survived 413 for treatment B is designated as FN, the treatment outcome of dead 413 for treatment A is designated as FP, and the treatment outcome of dead 413 for treatment B is designated as TN.

Next, the univariate analysis of block 107 (FIG. 1) is performed by calculating a support parameter SUP, an odds ratio OR, and a p-value of a Chi-Square test. With reference to FIG. 4, the support parameter SUP is equal to (TP+FP)/(TP+FP+FN+TN), and the odds ratio OR is equal to (FP*FN)/(TP*TN). The multivariate logistic regression of block 109 (FIG. 1) is then performed using a set of confounding factors $(x_1, x_2, \ldots x_n)$. An adjusted odds ratio AOR is equal to exp (βt) where log it (y)=β0+β1x1+β2x2+ . . . +βtxt.

One or more respective node-to-node links of FIG. 3 are associated with a corresponding set of parameters including the support parameter SUP, the odds ratio OR, and the p-value. For example, a first link between the first initial node 301 and the first combination node 311 is associated with a first parameter set 302 comprising SUP=0.60, OR=0.35, p<0.001, AOR=0.39, and p<0.001. Similarly, a second link between the second initial node 303 and the first combination node 311 is associated with a second parameter set 304 comprising SUP=0.60, OR=0.13, p<0.001, AOR=0.15, and p<0.001. Likewise, a third link between the first initial node 301 and the second combination node 313 is associated with a third parameter set 306 comprising SUP=0.35. A fourth link between the second initial node 303 and the third combination node 315 is associated with a fourth parameter set 308 comprising SUP=0.82, and OR=1.10. A fifth link between the fourth initial node 307 and the fourth combination node 317 is associated with a fifth parameter set 310 comprising SUP=0.62, OR=0.89, p<0.04, AOR=0.95, and p<0.07. A sixth link between the first combination node 311 and the fifth combination node 319 is associated with a sixth parameter set 312 comprising SUP=0.51, OR=0.78, p<0.001, AOR=0.87, p<0.002.

When generating each new combination node of FIG. 3, any nodes for therapies that are not of interest are pruned from the graph. For example, any node associated with a link having a support parameter SUP of less than a predetermined threshold is pruned from the graph. Alternatively or additionally, any node associated with a link having a univariate odds ratio OR greater than a predetermined threshold, or a p-value greater than a predetermined threshold, is pruned from the graph. Alternatively or additionally, any node associated with a link having a multivariate adjusted odds ratio AOR greater than a predetermined threshold, or a p-value greater than a predetermined threshold, is pruned from the graph. Alternatively or additionally, a node is pruned if one or more of its parent nodes have already been pruned from the graph.

Figure 5:
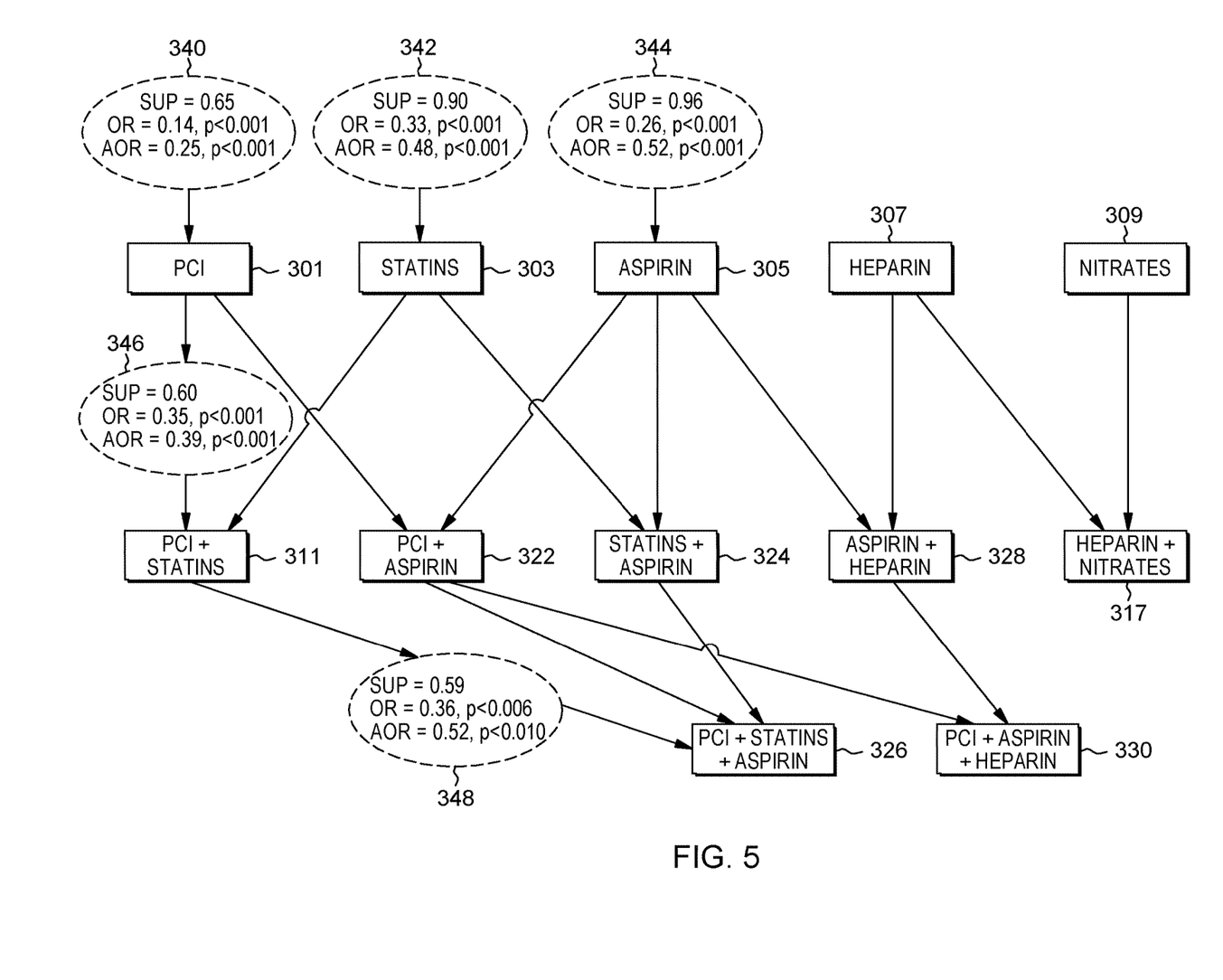
FIG. 5 illustrates an exemplary set of experimental results prepared using the method of FIG. 1 in accordance with one or more embodiments of the present invention.

FIG. 5 illustrates an exemplary set of experimental results prepared using the method of FIG. 1 in accordance with one or more embodiments of the present invention. An input dataset was employed that included data from approximately 16,000 patients, 1,000 deceased patients, and 20 different treatments. The predetermined threshold for SUP was set to 0.5, the predetermined threshold for OR was set to 1.0, and the predetermined threshold for p was set to 0.05. The output from the procedure of FIG. 1 included a set of combination therapies. A first set of nine size-one therapies was identified, where each size-one therapy included a single therapy. A second set of 17 size-two therapies were identified, where each size-two therapy included a combination of two therapies. A third set of 5 size-three therapies were identified, where each size-three therapy included a combination of three therapies.

The first initial node 301 of FIG. 5 was associated with a first parameter set 340 comprising SUP=0.65, OR=0.14, p<0.001, AOR=0.25, and p<0.001. The second initial node 303 of FIG. 5 was associated with a second parameter set 342 comprising SUP=0.90, OR=0.33, p<0.001, AOR=0.48, and p<0.001. The third initial node 305 of FIG. 5 was associated with a third parameter set 344 comprising SUP=0.65, OR=0.14, p<0.001, AOR=0.25, and p<0.001.

A set of combination nodes was constructed, including the first combination node 311, as well as a second combination node 322, a third combination node 324, a fourth combination node 326, a fifth combination node 328, and a sixth combination node 330. A first link between the first initial node 301 and the first combination node 311 was associated with a fourth parameter set 346 comprising SUP=0.60, OR=0.35, p<0.001, AOR=0.39, and p<0.001. A second link between the first combination node 311 and the fourth combination node 326 was associated with a fifth parameter set comprising SUP=0.59, OR=0.36, p<0.006, AOR=0.52, and p<0.010.

The graph of FIG. 5 was then searched to identify one or more combination therapies of interest from among the combination nodes 311, 322, 324, 326, 328, and 330. Given a set of treatments of interest, the graph is traversed. One or more combination nodes 311, 322, 324, 326, 328, and 330 associated with combination therapies that provide greater protection against a desired outcome than nodes associated with their parent therapies are selected. For example, a desired outcome may be a surviving patient as opposed to a deceased patient. Alternatively or additionally, a desired outcome may be a measured laboratory parameter, such as a blood test result or a level of low-density lipoproteins, falling within a desired range, or falling above or below a predetermined threshold, or changing in a desired direction as a result of the combination therapy.

Figure 6:
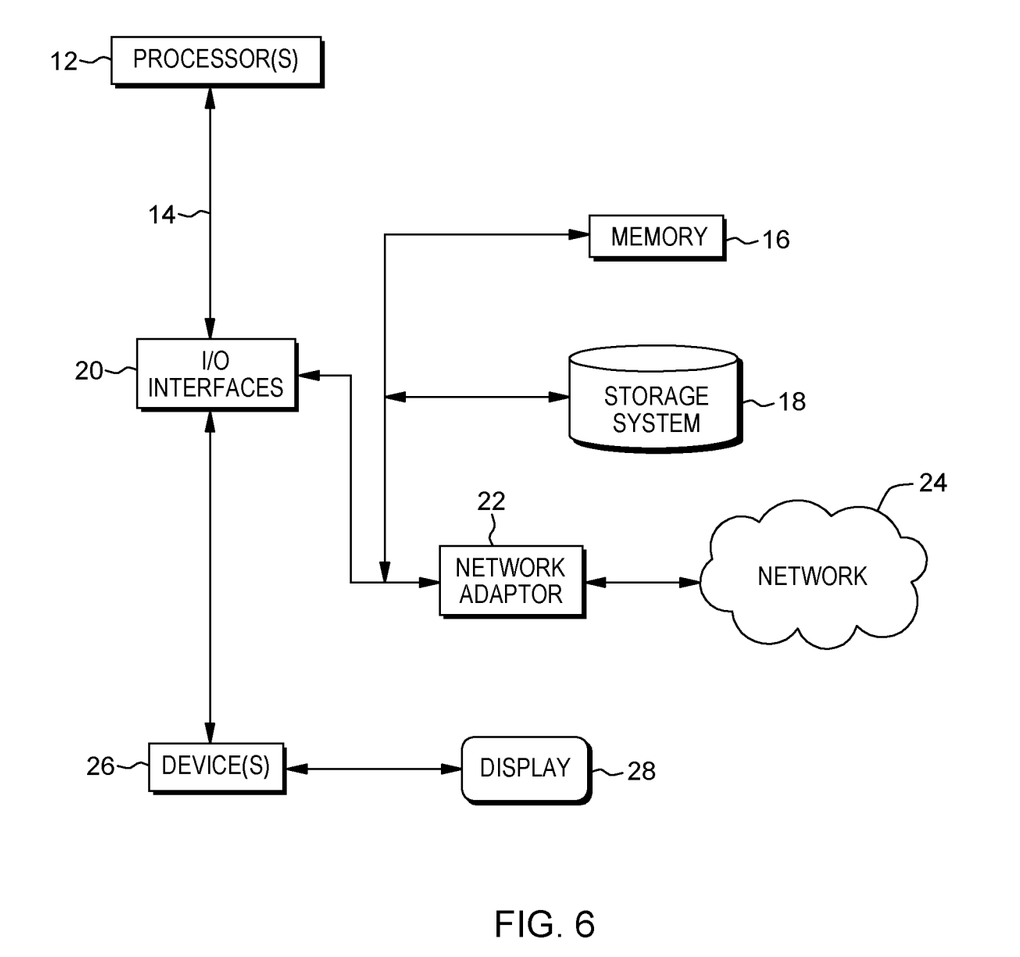
FIG. 6 illustrates an exemplary computer system for performing the method of FIG. 1 in accordance with one or more embodiments of the present invention.

FIG. 6 illustrates an exemplary computer system for performing the method of FIG. 1 in accordance with one or more embodiments of the present invention. This computer system is only one example of a suitable processing system and is not intended to suggest any limitation as to the scope of use or functionality of embodiments of the methodology described herein. The processing system shown may be operational with numerous other general-purpose or special-purpose computing system environments or configurations. Examples of well-known computing systems, environments, and/or configurations that may be suitable for use with the processing system shown in FIG. 6 may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system may be described in the general context of computer system executable instructions, such as program modules, being executed by a computer system. Generally, program modules may include routines, programs, objects, components, logic, data structures, and so on that perform particular tasks or implement particular abstract data types. The computer system may be practiced in distributed cloud computing environments where tasks are performed by remote processing devices that are linked through a communications network. In a distributed cloud computing environment, program modules may be located in both local and remote computer system storage media including memory storage devices.

The components of the computer system may include, but are not limited to, one or more processors or processing units 12, a system memory 16, and a bus 14 that couples various system components including system memory 16 to processor 12. The processor 12 may include a module 10 that performs the methods described herein. The module 10 may be programmed into the integrated circuits of the processor 12, or loaded from memory 16, storage device 18, or network 24 or combinations thereof.

Bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The computer system may include a variety of computer system readable media. Such media may be any available media that is accessible by computer system, and it may include both volatile and non-volatile media, removable and non-removable media.

System memory 16 can include computer system readable media in the form of volatile memory, such as random access memory (RAM) and/or cache memory or others. Computer system may further include other removable/non-removable, volatile/non-volatile computer system storage media. By way of example only, storage system 18 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

The computer system may also communicate with one or more external devices 26 such as a keyboard, a pointing device, a display 28, etc.; one or more devices that enable a user to interact with the computer system; and/or any devices (e.g., network card, modem, etc.) that enable the computer system to communicate with one or more other computing devices. Such communication can occur via Input/Output (I/O) interfaces 20.

Still yet, the computer system can communicate with one or more networks 24 such as a local area network (LAN), a general wide area network (WAN), and/or a public network (e.g., the Internet) via network adapter 22. As depicted, network adapter 22 communicates with the other components of computer system via bus 14. It should be understood that although not shown, other hardware and/or software components could be used in conjunction with the computer system. Examples include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A computer-implemented method comprising:
   receiving, at a hardware processor, a dataset associating each of a plurality of respective individual treatments with a corresponding outcome and a corresponding set of confounding factors;
   iteratively combining, at the hardware processor, a plurality of new potential combination therapies, the iterative combining comprising performing a breadth first search to construct a graph of nodes, and at each of a plurality of iterations, generating a node for a new potential combination therapy by adding one treatment to a therapy in a previous iteration or, when no previous iteration exists, adding an initial treatment to the therapy;
   using, by a hardware processor, the received dataset to automatically identify at least one candidate combination therapy of the new potential combination therapies that provides a statistically significantly greater protection against an outcome with reference to each of the plurality of respective individual treatments, including
   identifying a candidate for elimination from the plurality of new potential combination therapies; and
   pruning the candidate for elimination from the graph of nodes; and
   treating a patient with the identified at least one candidate combination therapy.

2. The computer-implemented method of claim 1, further comprising selecting a set of case and control patients from the received dataset for each of the plurality of new potential combination therapies.

3. The computer-implemented method of claim 2, further comprising performing a univariate analysis to compute a support parameter, an odds ratio, and a p-value for a Chi-square test, for each of the plurality of new potential combination therapies.

4. The computer-implemented method of claim 3, further comprising performing a multivariate logistic regression analysis with the set of confounding factors to compute an adjusted odds ratio and an adjusted p-value for a Wald test.

5. The computer-implemented method of claim 4, the identified candidate for elimination having at least one of: a low support parameter, a high odds ratio, or a high p-value, with respect to a corresponding set of predefined thresholds for one or more of: the support parameter, the odds ratio, or the p-value.

6. A computer program product comprising a non-transitory computer-readable storage medium having a computer-readable program stored therein, wherein the computer-readable program, when executed on a computing device including at least one processor, causes the at least one processor to perform:
   receiving a dataset associating each of a plurality of respective individual treatments with a corresponding outcome and a corresponding set of confounding factors;
   iteratively combining a plurality of new potential combination therapies, the iterative combining comprising performing a breadth first search to construct a graph of nodes, and at each of a plurality of iterations, generating a node for new potential combination therapy by adding one treatment to a therapy in a previous iteration or, when no previous iteration exists, adding an initial treatment to the therapy;
   using the received dataset to automatically identify at least one candidate combination therapy of the new potential combination therapies that provides a statistically significantly greater protection against an outcome with reference to each of the plurality of respective individual treatments, including
   identifying a candidate for elimination from the plurality of new potential combination therapies; and
   pruning the candidate for elimination from the graph of nodes; and
   treating a patient with the identified at least one candidate combination therapy.

7. The computer program product of claim 6, further configured for selecting a set of case and control patients from the received dataset for each of the plurality of new potential combination therapies.

8. The computer program product of claim 7, further configured for performing a univariate analysis to compute a support parameter, an odds ratio, and a p-value for a Chi-square test, for each of the plurality of new potential combination therapies.

9. The computer program product of claim 8, further configured for performing a multivariate logistic regression analysis with the set of confounding factors to compute an adjusted odds ratio and an adjusted p-value for a Wald test.

10. The computer program product of claim 9, the candidate for elimination having at least one of: a low support parameter, a high odds ratio, or a high p-value, with respect to a corresponding set of predefined thresholds for one or more of: the support parameter, the odds ratio, or the p-value.

11. A computer system comprising:
at least one processor; and
a memory coupled to the at least one processor, wherein the memory comprises program instructions which, when executed by the at least one processor, cause the at least one processor to perform:
receiving a dataset associating each of a plurality of respective individual treatments with a corresponding outcome and a corresponding set of confounding factors;
iteratively combining a plurality of new potential combination therapies, the iterative combining comprising performing a breadth first search to construct a graph of nodes, and at each of a plurality of iterations, generating a node for new potential combination therapy by adding one treatment to a therapy in a previous iteration or, when no previous iteration exists, adding an initial treatment to the therapy;
using the received dataset to automatically identify at least one candidate combination therapy of the new potential combination therapies that provides a statistically significantly greater protection against an outcome with reference to each of the plurality of respective individual treatments, including
identifying a candidate for elimination from the plurality of new potential combination therapies; and
pruning the candidate for elimination from the graph of nodes; and
treating a patient with the identified at least one candidate combination therapy.

12. The computer system of claim 11, further configured for selecting a set of case and control patients from the received dataset for each of the plurality of new potential combination therapies.

\* \* \* \* \*